US012805773B2

(12) United States Patent
Song et al.

(10) Patent No.: US 12,805,773 B2
(45) Date of Patent: Nov. 24, 2026

(54) PATCH-TYPE WEARABLE DEVICE

(71) Applicant: GWANGJU INSTITUTE OF SCIENCE AND TECHNOLOGY, Gwangju (KR)

(72) Inventors: Youngmin Song, Gwangju (KR); Minhyung Kang, Gwangju (KR); Gilju Lee, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 707 days.

(21) Appl. No.: 17/317,788

(22) Filed: May 11, 2021

(65) Prior Publication Data

US 2021/0345895 A1 Nov. 11, 2021

(30) Foreign Application Priority Data

May 11, 2020 (KR) ........................ 10-2020-0055598
Aug. 5, 2020 (KR) ........................ 10-2020-0098042

(51) Int. Cl.

| | |
|---|---|
| ***A61B 5/1455*** | (2006.01) |
| ***A61B 5/00*** | (2006.01) |
| ***A61B 50/00*** | (2016.01) |
| ***H04B 5/26*** | (2024.01) |
| ***H04B 5/70*** | (2024.01) |

(52) U.S. Cl.

CPC ........ *A61B 5/14552* (2013.01); *A61B 5/0004* (2013.01); *A61B 5/6833* (2013.01); *H04B 5/26* (2024.01); *H04B 5/70* (2024.01); *A61B 2050/0014* (2016.02)

(58) Field of Classification Search

CPC .... A61B 2050/0014; A61B 2560/0252; A61B 5/0004; A61B 5/02055; A61B 5/02416; A61B 5/14552; A61B 5/14557; A61B 5/6833; A61B 5/02427; A61B 5/02433; H04B 5/0031

See application file for complete search history.

(56) References Cited

U.S. PATENT DOCUMENTS 10,111,592 B2 10/2018 Shimuta
2016/0331252 A1* 11/2016 Matsuo ................ A61B 5/6803
2017/0323172 A1* 11/2017 Matthews .............. A61B 5/489

FOREIGN PATENT DOCUMENTS

JP 5692389 B2 4/2015
KR 20170133022 A * 12/2017

OTHER PUBLICATIONS

Jaehyun Choi et al., "Efficient NFC coil antennas for fully enclosed metallic-framed wearable devices," 2019, IET Microwaves, Antennas & Propagation, 14, pp. 211-214 (Year: 2019).*

(Continued)

*Primary Examiner* — Michael J Carey
*Assistant Examiner* — Maria Christina Talty
(74) *Attorney, Agent, or Firm* — Heidi Eisenhut; LOZA & LOZA, LLP

(57) ABSTRACT

A patch-type wearable device includes a circuit layer including a light emitting element and a light receiving element, a wireless communication module mounted on the circuit layer and configured to communicate with another device, and a passive radiation layer constituting an upper layer of the circuit layer and exhibiting passive radiation characteristics.

16 Claims, 10 Drawing Sheets

(56) References Cited

OTHER PUBLICATIONS

G. Wang et al., "Stretchable Optical Sensing Patch System Integrated Heart Rate, Pulse Oxygen Saturation, and Sweat pH Detection," IEEE Transactions on Biomedical Engineering, 66, pp. 1000-1005 (Year: 2019).*
G. Lee et al., "Colored, Daytime Radiative Coolers with Thin-Film Resonators for Aesthetic Purposes," Aug. 27, 2018, Advanced Optical Materials, 6, pp. 1800707 (Year: 2018).*
L. Dan et al., "Porous Polydimethylsiloxane-Silver Nanowire Devices for Wearable Pressure Sensors," 2019, ACS Applied Nano Materials, 2, 4869-4878 (Year: 2019).*
F. Burgoyne, "Adding colour to PMDS chips for enhanced contrast," Royal Society of Chemistry, Nov. 17, 2011 (Year: 2011).*
S. Yu et al., "Numerical study on the scattering property of porous polymer structures via supercritical CO2 microcellular foaming," May 10, 2020, Applied Optics, 59, pp. 4533-4541 (Year: 2020).*
Kim et al., "Battery-free, stretchable optoelectronic systems for wireless optical characterization of the skin", Sci. Adv. 2016; 2 : e1600418, Aug. 3, 2016. <http://advances.sciencemag.org/ on Jul. 2, 2021>.
Ku et al., "Multiscale porous elastomer substrates for multifunctional on-skin electronics with passive-cooling capabilities", PNAS, Jan. 7, 2020, vol. 117 no. 1 pp. 205-213 <www.pnas.org/cgi/doi/10.1073/pnas.1917762116>.
Mandal et al., "Hierarchically porous polymer coatings for highly efficient passive daytime radiative cooling", Science 362, pp. 315-319 Oct. 19, 2018 <http://science.sciencemag.org/>.
KR-10-2020-0098042. Korean Office Action mailed Aug. 30, 2021. (5 pages).

* cited by examiner

FIG. 5

| Polymer | Solvent | Non-solvent | Ratio |
|---|---|---|---|
| Cellulose acetate | acetone | Water | 1:10:1 |
| PMMA | acetone | Water | 1:10:1 |
| SEBS | Chloroform | IPA | 1:10:1 |
| P(VdF-HFP) | acetone | water | 1:10:1 |
| Polystyrene | tetrahydrofuran | water | 1:10:1 |
| Ethly-cellulose | ethanol | water | 1:10:1 |
| PLA | acetone | water | 1:10:1 |
| PLCL | acetone | water | 1:10:1 |
| PCL | acetone | water | 1:10:1 |

PATCH-TYPE WEARABLE DEVICE

CROSS-REFERENCE TO RELATED APPLICATIONS

The present application claims priority under 35 U.S.C. 119 and 35 U.S.C. 365 to Korean Patent Application Nos. 10-2020-0055598, filed on May 11, 2020, and 10-2020-0098042, filed on Aug. 5, 2020, which are hereby incorporated by reference in its entirety.

BACKGROUND

The present disclosure relates to a patch-type wearable device capable of improving a visible light reflection effect, a heat radiation effect, and light efficiency.

Recently, a technology for determining a user's health using a wearable device has appeared.

For example, a wearable device may include a light emitting diode (LED) and a photodiode. When light emitted from an LED passes through a skin and reaches a photodiode, information such as oxygen saturation and heart rate can be obtained using data obtained from the photodiode. As another example, a temperature sensor may be mounted on a wearable device to measure a user's temperature.

On the other hand, heat may be generated in a wearable device and heat may be transferred from a user's skin. Heat causes inaccuracy of data obtained from a wearable device. In particular, when a wearable device is used outdoors, more heat is generated due to absorption of sunlight. Thus, it is very difficult to obtain accurate data.

In addition, when a user uses a wearable device generating heat for a long period of time, it may cause a slight burn on a user's skin.

Therefore, there is a need for a means capable of effectively removing heat from a wearable device.

SUMMARY

Embodiments provide a patch-type wearable device capable of improving a visible light reflection effect, a heat radiation effect, and light efficiency.

According to one embodiment of the present disclosure, a patch-type wearable device includes a circuit layer including a light emitting element and a light receiving element, a wireless communication module mounted on the circuit layer and configured to communicate with another device, and a passive radiation layer constituting an upper layer of the circuit layer and exhibiting passive radiation characteristics.

In this case, the patch-type wearable device may further include an encapsulation layer disposed between the light emitting element and the light receiving element to block internal optical noise.

In this case, the encapsulation layer may constitute a lower layer of the circuit layer, and the light emitting element and the light receiving element may be mounted on the lower surface of the circuit layer.

In this case, the light emitting element and the light receiving element may be horizontally disposed, and the encapsulation layer may be positioned on a side of the light emitting element and a side of the light receiving element.

On the other hand, the patch-type wearable device may further include a controller configured to control the light emitting element to emit light, and transmit data obtained through the light receiving element to the another device through the wireless communication module.

In this case, the wireless communication module may be a near field communication (NFC) or BLUETOOTH™ module, the module may include a coil and a processor, and when the another device approaches, the NFC module may supply power induced through the coil to the controller. When the device adopts BLUETOOTH™ module, the device may require battery part.

On the other hand, the data may be used to determine at least one of oxygen saturation or heart rate.

On the other hand, the passive radiation layer may be made of a porous polymer and may exhibit passive radiation characteristics.

In this case, the porous polymer may include at least one of cellulose acetate, PMMA, SEBS, P(VdF-HFP), polystyrene, ethyl-cellulose, PLA, PLCL, or PCL. For example, the passivation radiation layer in which two or more porous polymers are laminated may be used.

On the other hand, the passive radiation layer may not include a metal heat sink.

According to one embodiment of the present disclosure, a patch-type wearable device includes a circuit layer including a light emitting element configured to emit light to a skin and a light receiving element configured to receive light emitted from the light emitting element, an encapsulation layer attached to the skin, and a passive radiation layer disposed on the circuit layer and exhibiting passive radiation characteristics.

The encapsulation layer may be disposed between the light emitting element and the light receiving element to block internal optical noise.

The patch-type wearable device 100 may include an upper layer, an intermediate layer, and a lower layer. The upper layer may include a passive radiation layer 200, the intermediate layer may include a circuit layer 300, and the lower layer may include an encapsulation layer 400.

The communication module may be a wireless near field communication (NFC) and BLUETOOTH™ module.

The passive radiation layer may include a polymer having a plurality of micro-scale or nano-scale pores.

The passive radiation layer may include a white porous polymer to increase passive radiation characteristics.

According to one embodiment of the present disclosure, a patch-type wearable device includes a circuit layer configured to sense a biometric signal adjacent to a skin, an encapsulation layer attached to the skin, and a passive radiation layer disposed on the circuit layer and including a plurality of pores to exhibit passive radiation characteristics.

The circuit layer may include a light emitting element and a light receiving element.

The encapsulation layer may be disposed between the light emitting element and the light receiving element.

The patch-type wearable device may further include a wireless communication module mounted on the circuit layer and configured to communicate with another device.

The passive radiation layer may not include a metal material and may include a polymer.

The details of one or more embodiments are set forth in the accompanying drawings and the description below. Other features will be apparent from the description and drawings, and from the claims.

BRIEF DESCRIPTION OF THE DRAWINGS

FIG. 5 is a view illustrating the ratio of a solvent, a non-solvent, and a polymer.

DETAILED DESCRIPTION OF THE EMBODIMENTS

Hereinafter, specific embodiments of the present disclosure will be described in detail with reference to the accompanying drawings. However, the spirit and scope of the present disclosure is not limited to the following embodiments. Those of ordinary skill in the art who understand the spirit and scope of the present disclosure will be able to easily propose other embodiments included within the scope of the same idea by adding, changing, deleting components. However, it will be said that this is also included within the sprit and scope of the idea of the present disclosure.

In the accompanying drawings, in describing the overall structure in order to easily express the spirit and scope of the present disclosure, the slight portions may not be expressed in detail. In describing the slight portions, the overall structure may not be reflected in detail. In addition, even when the specific parts such as the installation locations are different, the same name is given when the operation is the same, thereby improving the convenience of understanding. Furthermore, when there are a plurality of identical configurations, only one configuration will be described, and the same description will be applied to other configurations, and the description thereof will be omitted.

Figure 1A:
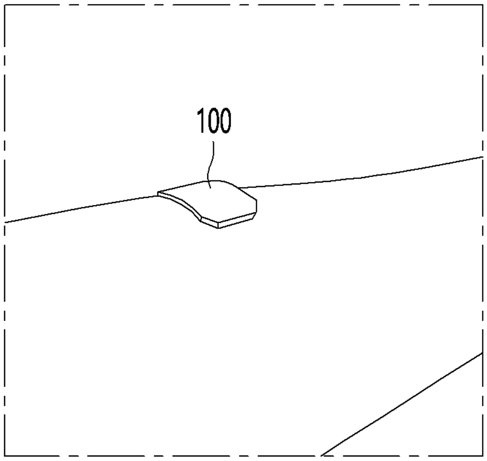
FIGS. 1(*a*), 1(*b*), and 1(*c*) are views for explaining a patch-type wearable device according to an embodiment of the present disclosure.
Figure 1B:
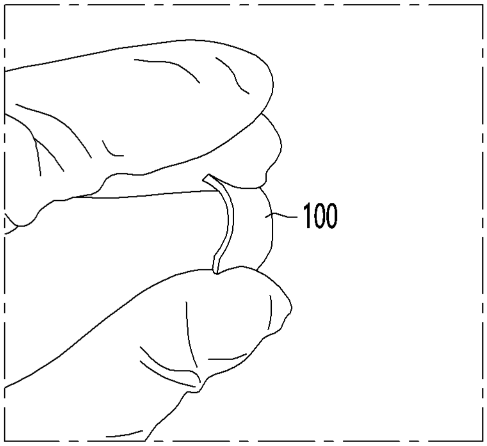
Figure 1C:
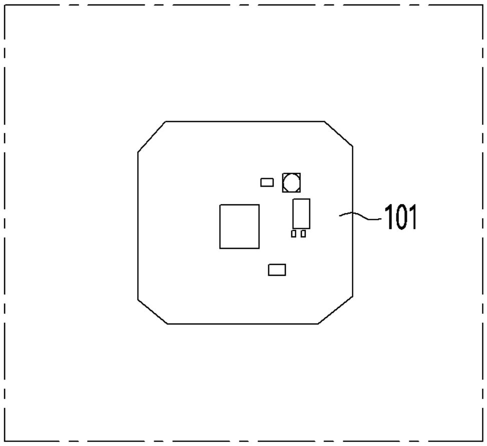

FIGS. 1(*a*), 1(*b*), and 1(*c*) are views for explaining a patch-type wearable device according to an embodiment of the present disclosure.

The patch-type wearable device 100 may have a thin patch shape, and may be attached to a skin at the time of use, as illustrated in FIG. 1(*a*). For example, the patch-type wearable device 100 may be attached to a person's arm whose skin is exposed.

In addition, as illustrated in FIG. 1(*b*), the patch-type wearable device 100 may have flexible characteristics in order to be attached to the skin. An adhesive component having adhesive strength may be applied to at least a portion of the lower surface of the patch-type wearable device 100.

Also, as illustrated in FIG. 1(*c*), a light emitting element and a light receiving element may be exposed on the lower surface 101 of the patch-type wearable device 100, and biometric data related to oxygen saturation, heart rate, and the like may be obtained through a light emitting module and a light receiving module. The lower surface 101 of the patch-type wearable device 100 may be a surface that is in contact with the skin.

In addition, a temperature sensing element may be exposed on the lower surface 101 of the patch-type wearable device 100, and data related to temperature may be obtained through the temperature sensing element.

Figure 2:
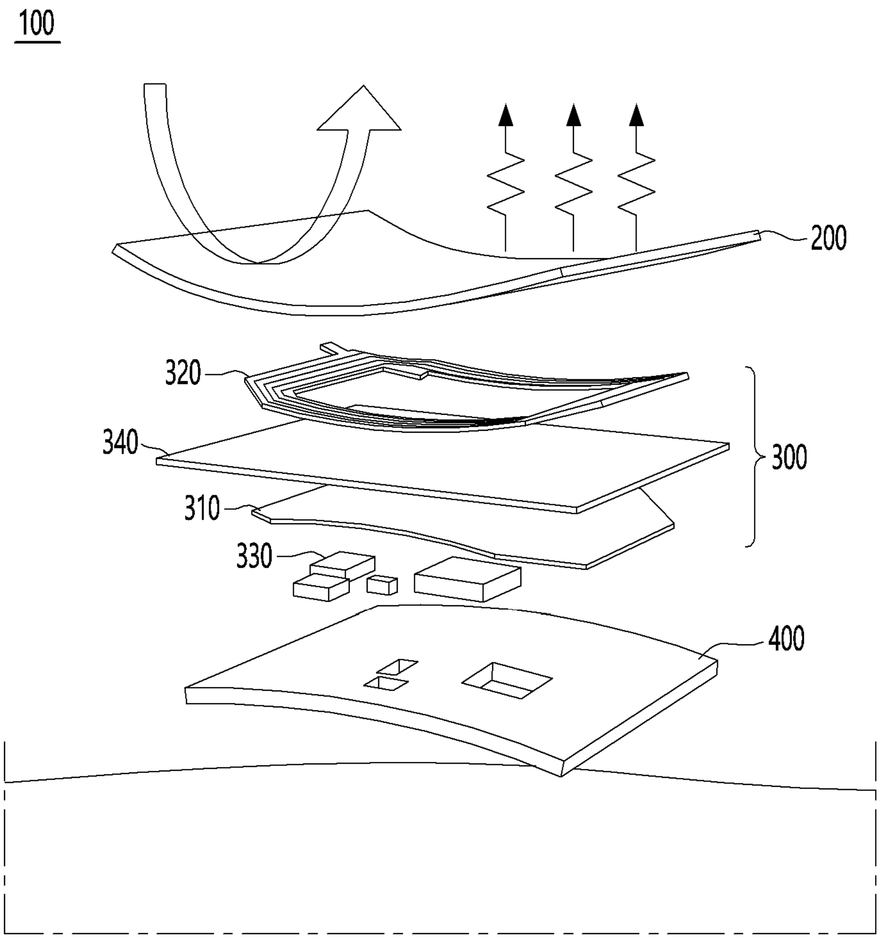
FIG. 2 is a view for explaining a configuration of a patch-type wearable device according to an embodiment of the present disclosure.

FIG. 2 is a view for explaining a configuration of a patch type wearable device according to an embodiment of the present disclosure.

As illustrated in FIG. 2, the patch-type wearable device 100 according to an embodiment of the present disclosure may be configured with a plurality of layers.

The patch-type wearable device 100 may include an upper layer, an intermediate layer, and a lower layer. The upper layer may include a passive radiation layer 100, the intermediate layer may include a circuit layer 300, and the lower layer may include an encapsulation layer 400.

The encapsulation layer 400 may constitute the lower portion of the circuit layer 300 and may be attached to a user's skin. In addition, a hole may be defined in the encapsulation layer 400, and a sensing element may be inserted into the hole.

Furthermore, the encapsulation layer 400 may have a black surface. To this end, the encapsulation layer 400 may be formed by mixing a black dye with a PDMS or applying a black dye to a PDMS.

The circuit layer 300 may be provided above the encapsulation layer 400 and below the passive radiation layer 200.

In addition, the circuit layer 300 may include a circuit board 310. The circuit board 310 may be a printed circuit board. In this case, the circuit configuration for the operation of the patch-type wearable device 100 may be patterned on the printed circuit board. Furthermore, the circuit configuration for the operation of the patch-type wearable device 100 may be patterned on the lower surface of the printed circuit board.

On the other hand, the circuit layer 300 may include a coil 320. The coil 320 may be disposed on the circuit board 310.

FIG. 2 illustrates that the coil 320 is mounted on the upper surface of the circuit board 310, but the present disclosure is not limited thereto.

For example, the coil may include an upper coil and a lower coil. The upper coil may be mounted on the upper surface of the circuit board 310, and the lower coil may be mounted on the lower surface of the circuit board 310.

On the other hand, the circuit layer 300 may include one or more sensing elements 330. The sensing element 330 may include at least one of a light emitting element, a light receiving element, or a temperature sensing element.

On the other hand, the sensing element 330 may be mounted on the lower surface of the circuit layer. In this case, the sensing element 330 may be inserted into the hole defined in the encapsulation layer 400. Therefore, the sensing element 330 may be in direct contact with the user's skin, or may be disposed to directly face the user's skin.

On the other hand, the circuit layer 300 may include a polyimide layer 340. The polyimide layer may prevent the coils from being connected to each other.

On the other hand, the passive radiation layer 200 may be provided on the circuit layer 300. In addition, the passive radiation layer 200 may exhibit passive radiation characteristics.

Figure 3:
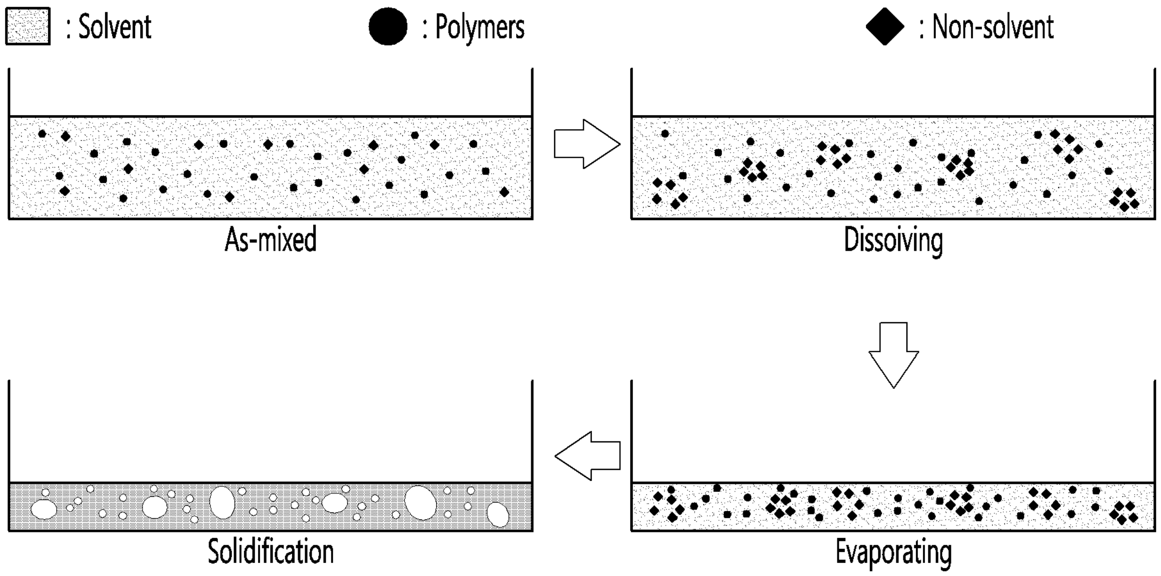
FIG. 3 is a view for explaining a method for manufacturing a passive radiation layer.
Figure 4:
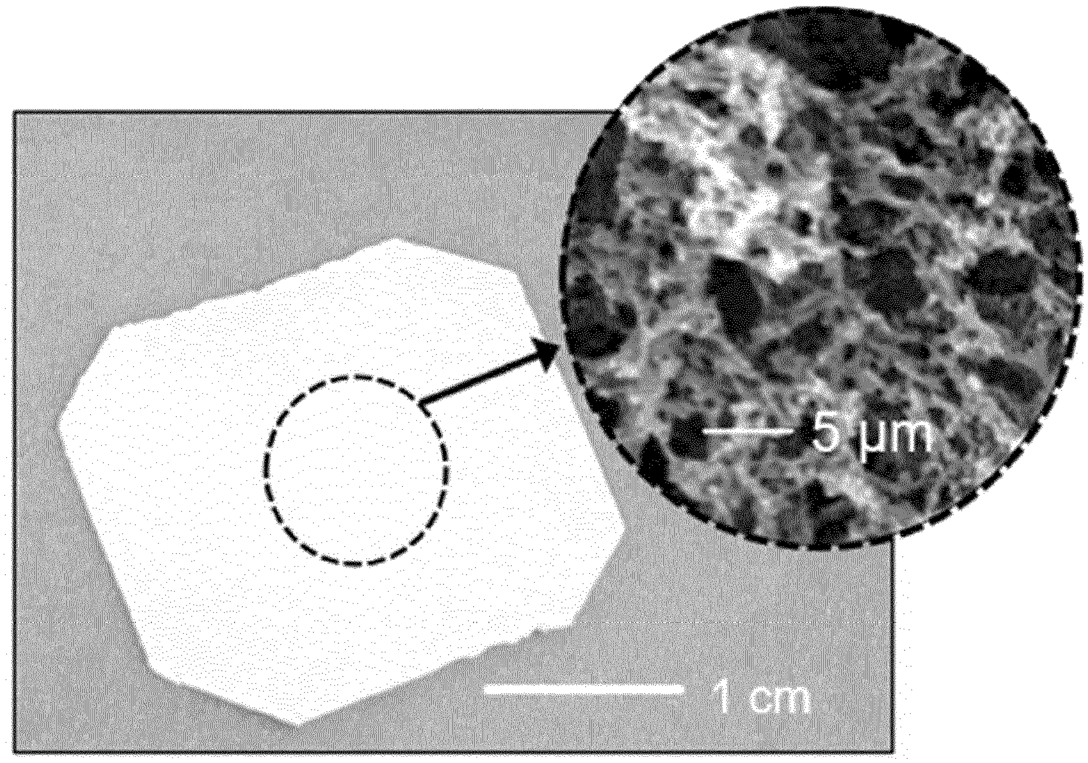
FIG. 4 is a view illustrating a porous polymer.

FIG. 3 is a view for explaining a method for manufacturing the passive radiation layer, and FIG. 4 is a view illustrating a porous polymer.

Referring to FIG. 3, when a solvent, a non-solvent, and a polymer, which are added at a certain ratio, are mixed in a single container for a long time, the polymer may be dissolved.

As time passes after the application of the solution, evaporating occurs in the mixed solution. In this case, the solution may be solidified. As the solvent evaporates, numerous pores (micro-scale pores or nano-scale pores) are formed.

The resulting porous polymer may exhibit passive radiation characteristics. Therefore, the porous polymer may be used as the passive radiation layer. FIG. 4 illustrates the porous polymer.

FIG. 5 is a view illustrating the ratio of the solvent, the non-solvent, and the polymer.

As the polymer, at least one of cellulose acetate, PMMA, SEBS, P(VdF-HFP), polystyrene, ethyl-cellulose, PLA, PLCL, or PCL may be used. For example, a passive radiation layer in which two or more porous polymers are laminated may be used.

A corresponding solvent (one of acetone, chloroform, tetrahydrofuran, and ethanol) may be used for each polymer, and water and IPA may be used as the non-solvent.

In addition, the ratio of the polymer, the solvent, and the non-solvent may be 1:10:1.

On the other hand, when there is no process of forming the pores as described above, the polymer may have a transparent color. However, when a plurality of pores are formed through the above-described process, the pores may scatter light. Therefore, the porous polymer may have a white color, and may have a high reflectance for light. In addition, the porous polymer may exhibit high emissivity in a long infrared band.

Figure 6:
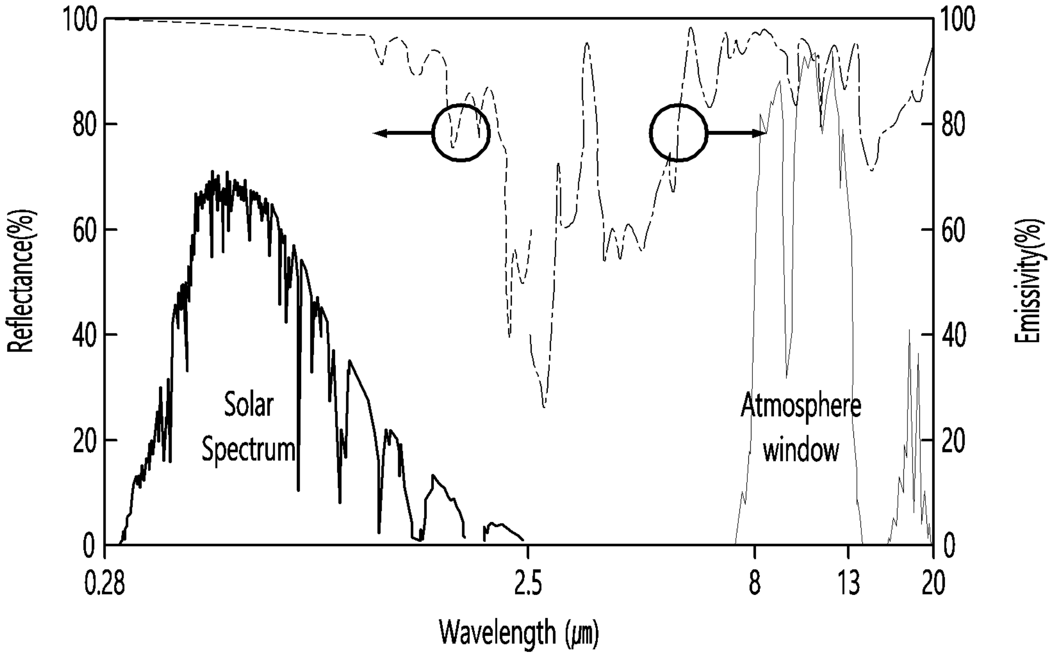
FIG. 6 is a view for explaining passive radiation characteristics of a porous polymer.

FIG. 6 is a view for explaining passive radiation characteristics of the porous polymer.

The passive radiation structure is a device for lowering a temperature without supplying external power, and is attracting attention as an ultra-power saving/eco-friendly technology because it can lower a temperature by minimizing power consumption.

A passive radiation cooling structure is a technology that is clearly distinguished from a conduction and convection method that induces thermal equilibrium. In particular, recently, studies on passive radiation cooling structures that can be used not only at night but also during the day are being actively conducted in developed countries.

The passive radiation cooling structure for daytime use has to strongly reflect sunlight and effectively radiate internal heat into the outer space in the form of electromagnetic waves. Therefore, the ideal radiation cooling structure has to reflect light of a wavelength in a solar spectrum as much as possible, and emit electromagnetic waves in a long infrared band (about 4 μm to 20 μm) including an atmosphere window as much as possible.

The passive radiation layer according to the present disclosure may have passive radiation characteristics having a high emissivity in a long infrared band (about 4 μm to 20 μm) (especially in an atmosphere window), compared to a surrounding band, and having a high reflectance in a solar spectrum, compared to a surrounding band.

The passive radiation layer according to the present disclosure has a reflectance close to 100% in a visible light band and a very high emissivity (about 80% or more) even in a long infrared band, thereby effectively dissipating heat.

In addition, the passive radiation layer according to the present disclosure may have cooling characteristics through passive radiation without cooling the device through conduction of a metal thin-film heat sink.

Specifically, when a metal heat sink is used for cooling an element, interference may occur in a coil disposed therebelow. Therefore, in the present disclosure, cooling characteristics may be exhibited through passive radiation by forming the porous polymer, without exhibiting device cooling characteristics through conduction by forming a metal into a thin film. Therefore, it is possible to prevent the occurrence of performance degradation of the NFC frequency.

Figure 7:
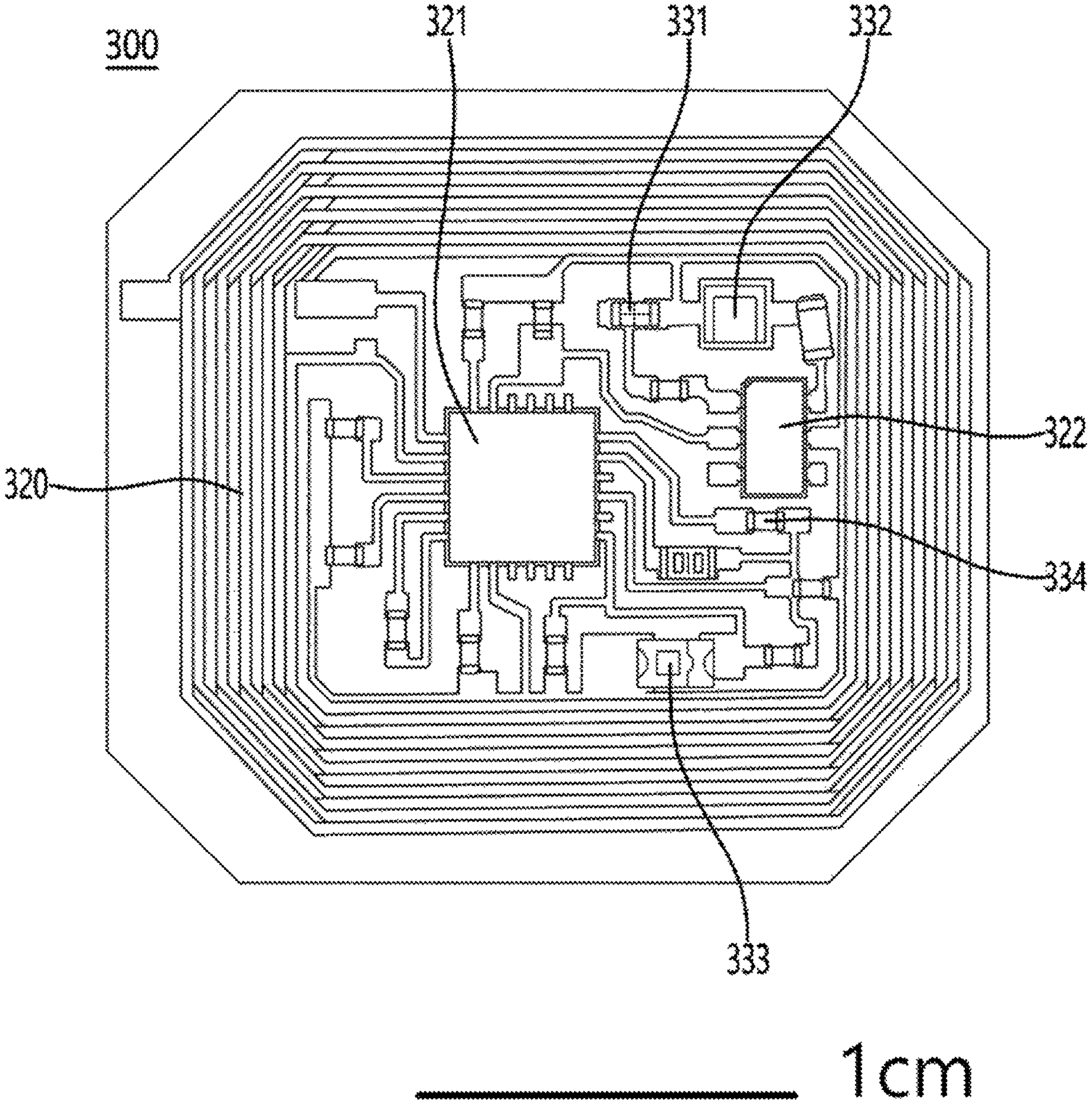
FIG. 7 is a view illustrating a lower portion of a circuit layer.

FIG. 7 is a view illustrating the lower portion of the circuit layer.

The circuit layer 300 may include a wireless communication module, one or more sensing elements, and a controller.

The wireless communication module may be mounted on the circuit layer and may transmit/receive data by performing communication with other devices.

The wireless communication module may communicate with other devices through a communication method such as BLUETOOTH™ or WI-FI™. In this case, the patch-type wearable device may include a battery for supplying power to the wireless communication module.

On the other hand, the wireless communication module may be a near field communication (NFC) module. In this case, the wireless communication module may perform short-range wireless communication with an external device.

The NFC module may include a coil 320 and an NFC processor 321.

On the other hand, the NFC module may receive power from an external device. Specifically, when another device performing wireless power transmission approaches, the NFC module may supply power induced through the coil to the controller 322.

In addition, the NFC module may transmit data to an external device. Specifically, the controller 322 may drive the light emitting element, and data obtained from the sensing element may be transmitted to the NFC module. In this case, the NFC module can transmit data to an external device through short-range wireless communication. The external device may be a mobile terminal such as a smart phone.

On the other hand, at least one sensing element may include light emitting elements 331 and 332, a light receiving element 333, and a temperature sensing element 334.

The one or more light emitting elements 331 and 332 may be elements that emit light, and may be, for example, LEDs.

In addition, the light receiving element 333 may be an element that receives light emitted from the light emitting elements 331 and 332, and may be, for example, a photodiode.

In addition, the temperature sensing element 334 may be an element capable of sensing a temperature of a skin, and may be, for example, a thermistor.

On the other hand, when power is supplied, the controller 322 may control the light emitting element to emit light, and may transmit data obtained through the light receiving element to another device through the wireless communication module. The obtained data may be used to determine oxygen saturation and heart rate.

In addition, when power is supplied, the controller 322 may transmit data obtained from the temperature sensing element 334 to another device through the wireless communication module. The obtained data may be used to determine a temperature of a skin.

Figure 8:
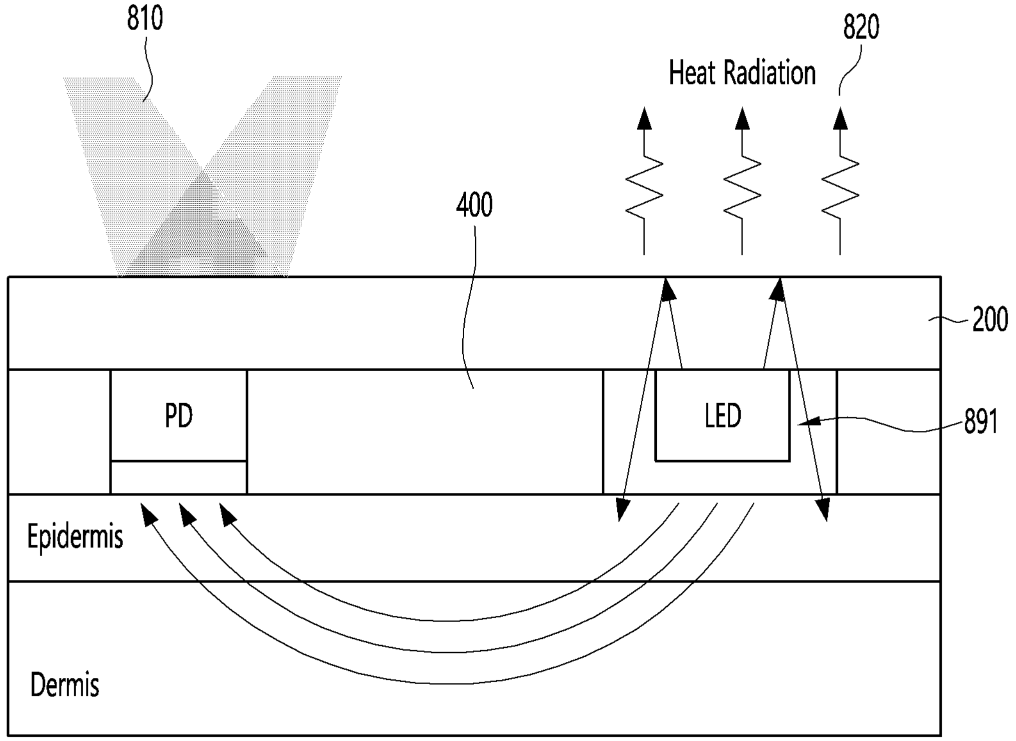
FIG. 8 is a cross-sectional view of a patch-type wearable device.

FIG. 8 is a cross-sectional view of the patch type wearable device.

All or part of the encapsulation layer 400 may be disposed between the light emitting element LED and the light receiving element PD to block internal optical noise.

Specifically, in order to obtain biometric information such as oxygen saturation and heart rate, light emitted from the light emitting element LED must pass through the skin and enter the light receiving element PD.

However, when the light emitted from the light emitting element LED moves to the light receiving element PD without passing through the skin (for example, when light moves from the light emitting element LED to the light receiving element PD in a straight line, or when light is reflected from the passive radiation layer 200 and then moves to the light receiving element PD), the accuracy of data may be degraded. The light moving to the light receiving element PD without passing through the skin may be referred to as optical noise.

Therefore, all or part of the encapsulation layer 400 may be disposed between the light emitting element LED and the light receiving element PD to absorb internal optical noise (light moving from the light emitting element LED to the light receiving element PD in a straight line, and light that is reflected from the passive radiation layer 200 and moves to the light receiving element PD). In order to increase the efficiency of light absorption, the encapsulation layer 400 may be formed in black.

On the other hand, both the light emitting element LED and the light receiving element PD may be mounted on the lower surface of the circuit board. Therefore, the light emitting element LED and the light receiving element PD may be horizontally disposed. Therefore, the encapsulation layer 400 may be disposed on the side of the light emitting element LED and the side of the light receiving element PD and may be disposed between the light emitting element LED and the light receiving element PD, thereby effectively blocking internal optical noise.

On the other hand, the encapsulation layer 400 may be entirely formed under the circuit layer 300 as well as between the light emitting element LED and the light receiving element PD. In this case, one or more holes may be defined in the encapsulation layer 400, and one or more sensing elements may be respectively inserted into the one or more holes.

On the other hand, it has been described above that the passive radiation layer has a high reflectance in the visible light band. These characteristics may be effective in blocking noise caused by external light 810.

That is, the passive radiation layer 200 reflects the external light 810, thereby preventing data from being distorted due to the external light 810 entering the light receiving element.

In addition, the passive radiation layer 200 may have a high reflectance even for visible light emitted from the light emitting element LED. Therefore, the passive radiation layer 200 may reduce optical loss and increase light efficiency.

Specifically, a space 891 may be defined between the light emitting element LED and the encapsulation layer 400. The light emitted from the light emitting element LED may be reflected by the passive radiation layer 200 having a high reflectance, move to the skin, pass through the skin, and then enter the light receiving element PD.

That is, the encapsulation layer 400 and the passive radiation layer 200 may block internal optical noise and external optical noise and reduce optical loss. Therefore, the measurement performance of the wearable device using optoelectronics may be improved.

On the other hand, the passive radiation layer 200 may reflect the external visible light 810 with a high reflectance to prevent heat from being generated by absorption of external light. In addition, the passive radiation layer 200 may effectively dissipate heat 820 generated between the wearable device and the skin to the outside with a high emissivity.

In addition, due to passive radiation characteristics, no batteries are used for cooling. Therefore, the present disclosure has an advantage of being able to effectively perform the role of the cooler even in a wearable device that does not use a battery. Accordingly, there is an advantage that can contribute to weight reduction and miniaturization of the patch-type wearable device.

Figure 9:
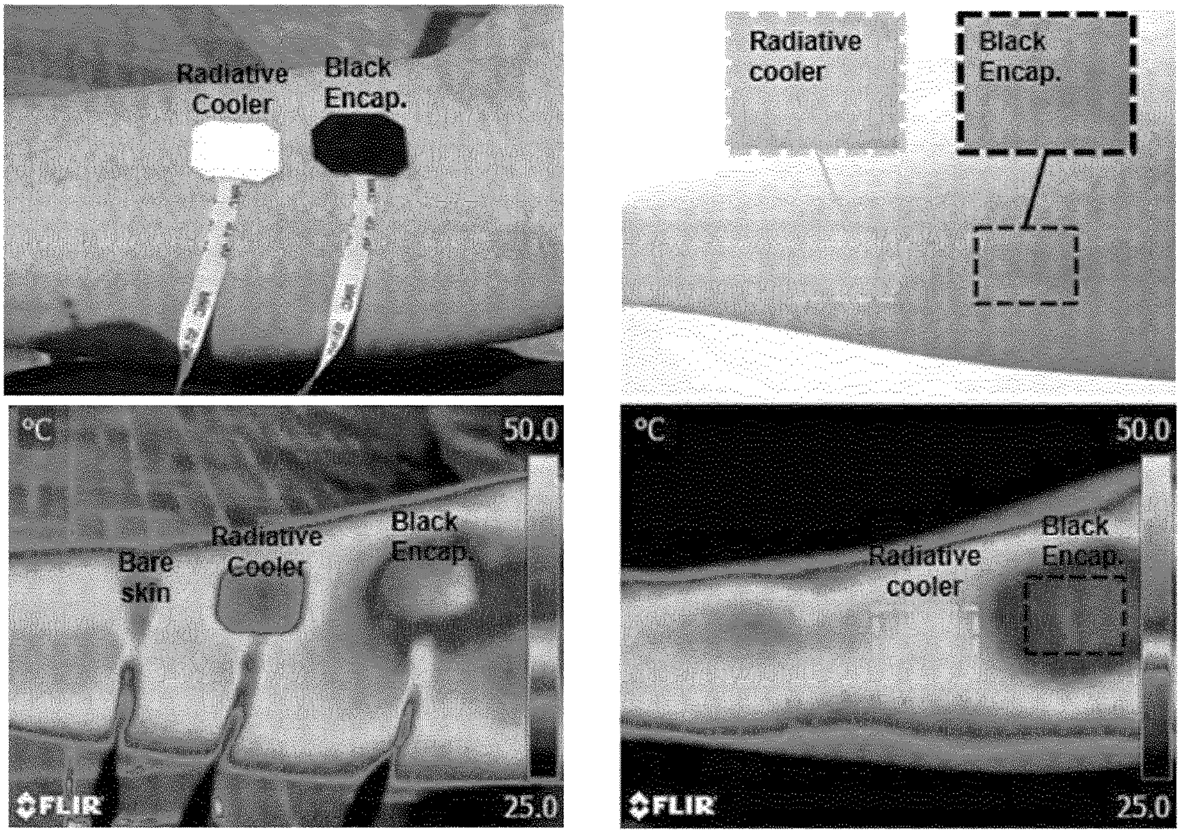
FIGS. 9 and 10 are experimental results of comparing a patch-type wearable device according to the present disclosure with a wearable device covered with a black encapsulation layer so as to block external optical noise.
Figure 10:
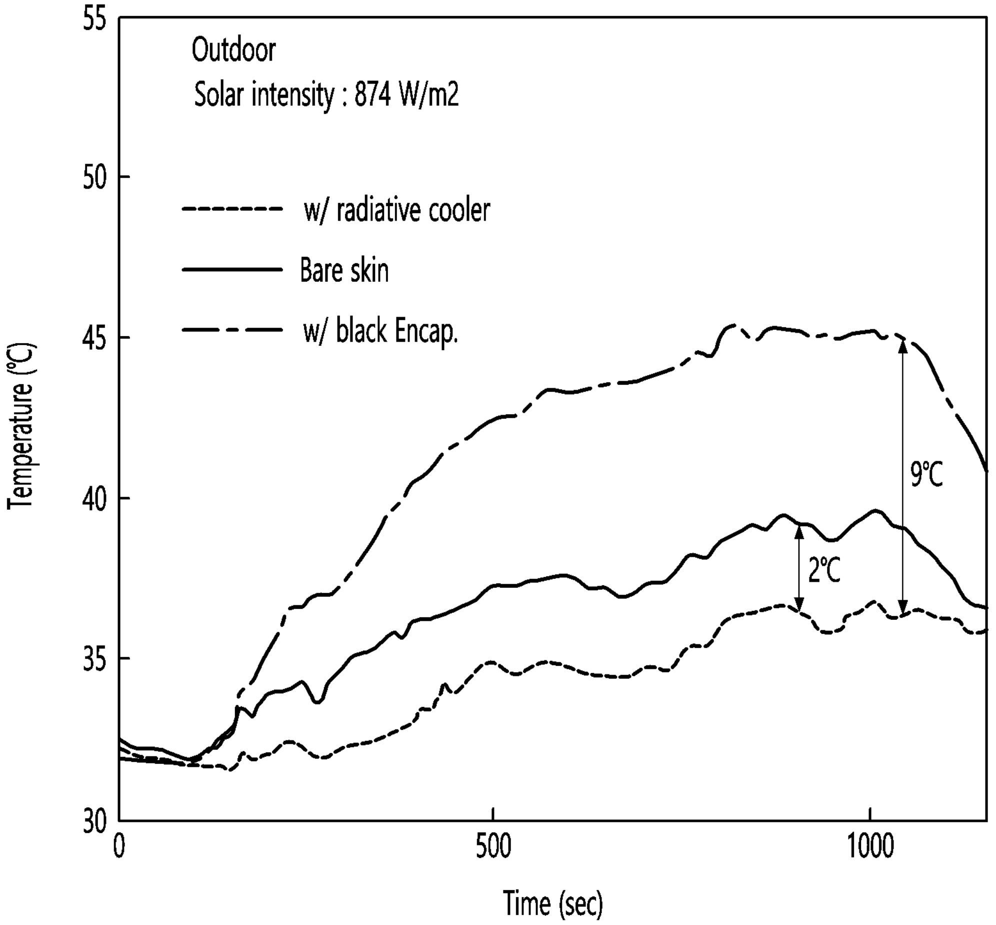

FIGS. 9 and 10 are experimental results of comparing the patch-type wearable device according to the present disclosure with the wearable device covered with the black encapsulation layer so as to block external optical noise.

In the wearable device covered with the black encapsulation layer in order to block external optical noise, the temperature of the wearable device may increase because the black encapsulation layer absorbs external light. Accordingly, it was confirmed that the temperature increased to a maximum of 45 °C, and it was confirmed that the skin turned red.

However, it was confirmed that the patch-type wearable device (radiative cooler) according to the present disclosure exhibited a temperature of 9 °C lower than that of the wearable device covered with the black encapsulation layer at the same time zone, and the temperature was lower than the temperature of the bare skin.

Figure 11:
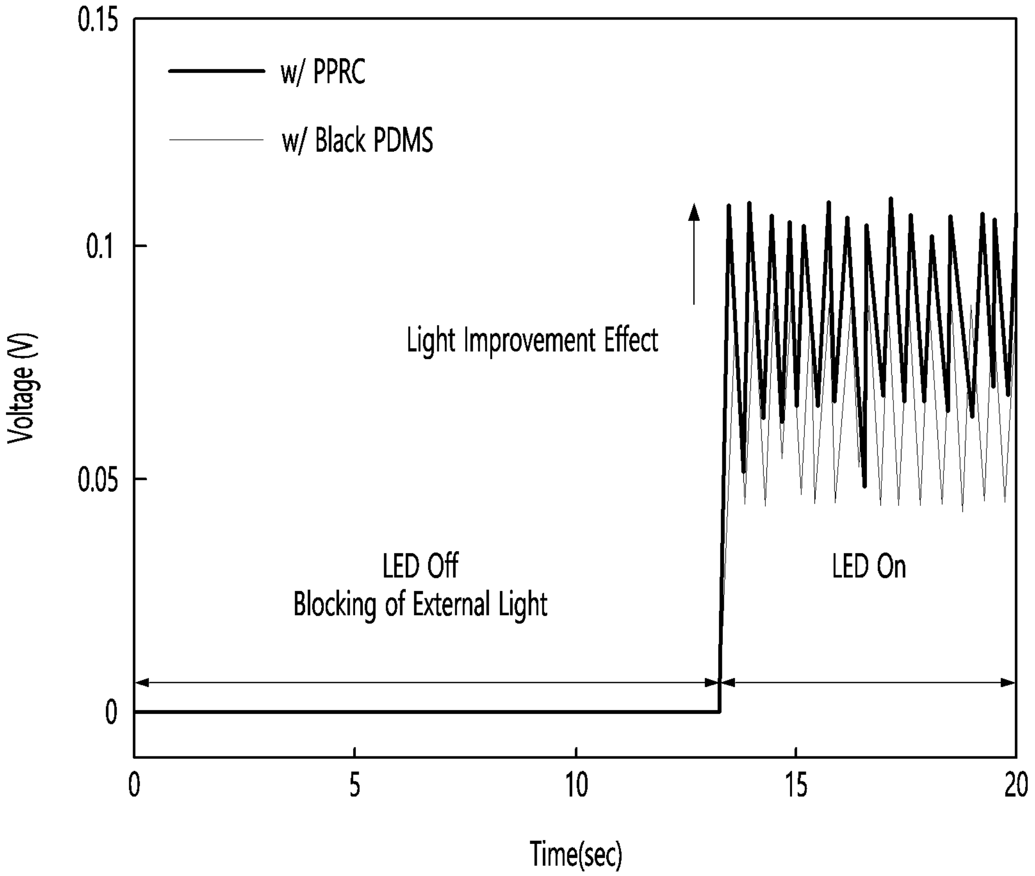
FIG. 11 is a view illustrating an effect of improving light efficiency.

FIG. 11 is a view illustrating an effect of improving light efficiency.

It can be seen that the patch-type wearable device (PPRC) including the passive radiation layer and the encapsulation layer exhibits a higher light improvement effect than the wearable device (black PDMS) in which the encapsulation layer is simply provided with a black PDMS.

As described above, according to the present disclosure, it is possible to implement the patch-type wearable device having a high data measurement accuracy, a small size, and a light weight. With a simple operation of bringing an external device (such as a mobile phone) closely, it is possible to easily measure biometric signals (oxygen saturation, heart rate, body temperature, etc.), and the reliability of the measurement can also be improved.

Therefore, there is an advantage of increasing portability and reducing inconvenience caused by attaching the wearable device.

In addition, it is possible to prevent skin damage and device deterioration problems caused by device heat generation when exposed outdoors for a long time, to reduce indoor and outdoor temperature measurement errors, and to increase the reliability of body temperature measurement of the temperature sensor.

The detailed description should not be construed as limiting the present disclosure in all respects and should be considered as illustrative. The scope of the present disclosure should be determined by rational interpretation of the appended claims, and all modifications within the equivalent scope of the present disclosure fall within the scope of the present disclosure.

What is claimed is:

1. A patch-type wearable device comprising:

a circuit layer including a light emitting element and a light receiving element;

a wireless communication module mounted on the circuit layer and configured to communicate with another device; and a passive radiation layer constituting an upper layer of the circuit layer and exhibiting passive radiation characteristics having a high emissivity in a long infrared band of 4 to 20 μm and having a high reflectance in a solar spectrum, in order that the passive radiation layer has cooling characteristics in order to cool the patch-type wearable device without forming a metal thin film and without providing a battery to cool the patch-type wearable device, wherein the passive radiation layer includes a first portion of the passive radiation layer corresponding with the light emitting element and a second portion of the passive radiation layer corresponding with the light receiving element, and wherein the passive radiation layer comprises a porous polymer having a plurality of pores that scatter visible light to exhibit a white appearance, the porous polymer including at least one of cellulose acetate, Polymethylmethacrylate (PMMA), Styrene Ethylene Butylene Styrene (SEBS), poly(vinylidenefluoride-co-hexafluoropropylene) (P(VdF-HFP)), polystyrene, ethyl-cellulose, polylactic acid (PLA), Poly(lactide-co-ε-caprolactone) (PLCL), or poly(ε-caprolactone) (PCL).

2. The patch-type wearable device of claim 1, further comprising an encapsulation layer disposed between the light emitting element and the light receiving element to block internal optical noise.

3. The patch-type wearable device of claim 2, wherein the encapsulation layer constitutes a lower layer of the circuit layer, and wherein the light emitting element and the light receiving element are mounted on the lower surface of the circuit layer.

4. The patch-type wearable device of claim 3, wherein the light emitting element and the light receiving element are horizontally disposed, and wherein the encapsulation layer is positioned on a side of the light emitting element and a side of the light receiving element.

5. The patch-type wearable device of claim 2, comprising a hole provided in the encapsulation layer, wherein the light emitting element is provided in the hole, and a space between the light emitting element and a lateral surface of the hole so as that a light of the light emitting element is reflected from the passive radiation layer and passes through the space in order to enter the skin.

6. The patch-type wearable device of claim 1, further comprising a controller configured to control the light emitting element to emit light, and transmit data obtained through the light receiving element to the another device through the wireless communication module.

7. The patch-type wearable device of claim 6, wherein the wireless communication module is a near field communication (NFC) module, wherein the NFC module includes a coil and an NFC processor, and wherein, when the another device approaches, the NFC module supplies power induced through the coil to the controller.

8. The patch-type wearable device of claim 6, wherein the data is used to determine at least one of oxygen saturation or heart rate.

9. The patch-type wearable device of claim 1, wherein the passive radiation layer does not include a metal heat sink.

10. A patch-type wearable device comprising:

a circuit layer including a light emitting element configured to emit light to a skin and a light receiving element configured to receive light emitted from the light emitting element;

a wireless communication module mounted on the circuit layer and configured to communicate with another device;

an encapsulation layer attached to the skin, wherein the encapsulation layer is disposed between the light emitting element and the light receiving element to block internal optical noise; and a passive radiation layer disposed on the circuit layer and exhibiting passive radiation characteristics having a high emissivity in a long infrared band of 4 to 20 μm and having a high reflectance in a solar spectrum, in order that the passive radiation layer has cooling characteristics in order to cool the patch-type wearable device without forming a metal thin film and without providing a battery to cool the patch-type wearable device, wherein the passive radiation layer includes at least two portions among a first portion of the passive radiation layer corresponding with the light emitting element, a second portion of the passive radiation layer corresponding with the light receiving element, and a third portion of the passive radiation layer corresponding with the encapsulation layer, wherein the passive radiation layer comprises a porous polymer having a plurality of pores that scatter visible light to exhibit a white appearance.

11. The patch-type wearable device of claim 10, wherein the communication module is a wireless near field communication (NFC) module.

12. The patch-type wearable device of claim 10, wherein the passive radiation layer includes a polymer having a plurality of micro-scale or nano-scale pores.

13. The patch-type wearable device of claim 10, wherein the passive radiation layer includes a white porous polymer.

14. A patch-type wearable device comprising:

a circuit layer configured to sense a biometric signal adjacent to a skin;

a wireless communication module mounted on the circuit layer and configured to communicate with another device;

an encapsulation layer attached to the skin; and a passive radiation layer disposed on the circuit layer and including a plurality of pores to exhibit passive radiation characteristics by scattering light, wherein the circuit layer includes a light receiving element, wherein the passive radiation layer includes at least a portion of the passive radiation layer corresponding with the light receiving element, wherein the passive radiation characteristics have a high emissivity in a long infrared band of 4 to 20 μm and having a high reflectance in a solar spectrum, in order that the passive radiation layer has cooling characteristics in order to cool the patch-type wearable device without forming a metal thin film to cool the patch-type wearable device and without providing a battery to cool the patch-type wearable device, wherein the passive radiation layer comprises a porous polymer having a plurality of pores that scatter visible light to exhibit a white appearance.

15. The patch-type wearable device of claim 14, wherein the circuit layer further includes a light emitting element, and wherein the encapsulation layer is disposed between the light emitting element and the light receiving element.

16. The patch-type wearable device of claim 14, wherein the passive radiation layer does not include a metal material and includes a polymer.

* * * * *